United States Patent [19]

Shim et al.

[11] 3,965,217

[45] June 22, 1976

[54] METHOD OF PREPARING STABLE CONDENSATION PRODUCTS AND PRODUCTS FORMED BY THE PROCESS

[75] Inventors: Kyung S. Shim, Irvington; Edward N. Walsh, New City, both of N.Y.

[73] Assignee: Stauffer Chemical Company, Westport, Conn.

[22] Filed: Aug. 5, 1974

[21] Appl. No.: 494,444

[52] U.S. Cl. .......................... 260/928; 260/2.5 AJ; 260/2.5 AR; 260/45.7 P; 260/927 R; 260/978; 260/982; 260/983; 260/990
[51] Int. Cl.$^2$ ....................... C07F 9/09; C07F 9/40
[58] Field of Search ................ 260/927 R, 928, 982, 260/989, 990

[56] References Cited
UNITED STATES PATENTS

| | | | |
|---|---|---|---|
| 3,641,202 | 2/1972 | Biranowski et al. | 260/928 X |
| 3,855,359 | 12/1974 | Weil | 260/928 |
| 3,822,327 | 7/1974 | Weil | 260/928 |
| 3,896,187 | 7/1975 | Weil | 260/928 |

FOREIGN PATENTS OR APPLICATIONS

| | | | |
|---|---|---|---|
| 1,202,501 | 10/1965 | Germany | 260/982 |

*Primary Examiner*—Richard L. Raymond
*Attorney, Agent, or Firm*—Richard P. Fennelly

[57] ABSTRACT

Stabilized products which are phosphorus containing oligomers having -O-C-C-O- linkages between phosphorus atoms and which are obtained by the self-condensation of β-haloalkyl esters of pentavalent phosphorus acids or the condensation products of these esters with an alkyl ester of a pentavalent phosphorus acid are formed by terminating the condensation reaction when it is about 35–75% complete, said condensation being performed in the absence of a nucleophilic initiator, such as a sodium salt initiator. The lower degree of condensation in the product and the absence of the nucleophilic initiator during the condensation reaction, is responsible for the lesser degree of scorching in a polyurethane foam containing the product as compared to one which is formed by allowing the condensation reaction go to completion or by use of a nucleophilic initiator during the condensation. If desired, the final product can be post-treated with an alkylene oxide and/or water or alcohol or by extraction with an inert organic solvent.

9 Claims, No Drawings

METHOD OF PREPARING STABLE CONDENSATION PRODUCTS AND PRODUCTS FORMED BY THE PROCESS

TECHNICAL DESCRIPTION OF THE INVENTION

The present invention is a process for forming improved condensation products of β-haloalkyl esters of pentavalent phosphorus acids which have flame retardant properties. A number of processes for formation of the class of compounds of interest herein are described in the patent literature and in copending applications including the following.

1. U.S. Pat. No. 3,513,644 to Edward D. Weil which describes the preparation of polycondensed oligomeric phosphates by heating of tris(2-haloalkyl) phosphates;
2. U.S. Pat. Nos. 3,641,202 and 3,695,925 to Edward D. Weil which describe the preparation of oligomeric polycondensed phosphonates from bis(-haloalkyl) vinylphosphonates;
3. U.S. Pat. No. 3,896,187 of Edward D. Weil which describes liquid poly(haloethyl-ethyleneoxy) phosphoric acid esters prepared by condensing tris(2-haloethyl) phosphate;
4. U.S. Ser. No. 410,583, filed Nov. 12, 1973, now abandoned, and U.S. Pat. No. 3,855,359 of Edward D. Weil which describe the copolycondensation of certain phosphates and phosphonates having a 2-haloalkyl group on at least one of these reactants;
5. U.S. Pat. No. 3,822,327 of Edward D. Weil which describes homo- and co-polycondensates of bis(2-haloethyl) vinylphosphonates; and
6. U.S. Pat. No. 3,891,727, of Edward D. Weil which relates generally to condensation products of haloalkyl esters of pentavalent phosphorus acids.

These patents and disclosures insofar as they relate to the condensation products usable in the practice of the instant invention are incorporated herein by reference. The term "condensation product of a β-haloalkyl ester of a pentavalent phosphorus acid" as used herein includes condensation products produced either by self-condensation reactions of such esters or a condensation reaction of such a β-haloalkyl ester with other alkyl esters of pentavalent phosphorus acids. Included within this definition are the condensation products described in U.S. Pat. No. 3,764,640 to Klose.

The process of this invention is particularly applicable to the homopolymerization product of tris(2-chloroethyl) phosphate, to the copolycondensation product of bis(2-chloroethyl)vinylphosphate and dimethyl methylphosphonate, to the copolycondensation product of bis(2-chloroethyl) vinylphosphonate and trimethyl phosphate, to the homopolycondensation product of bis(2-chloroethyl) vinylphosphonate, and to the copolycondensation product of tris(2-chloroethyl)-phosphate and dimethyl methylphosphonate.

Briefly, the polycondensation products are produced by reacting the monomer (both of which, as has already been noted, may be the same) to give off a volatile alkyl halide or alkylene dihalide and leave behind a non-volatile oligomeric condensation product. The reaction can be carried out in an inert organic solvent, such as benzene, ethylene dichloride, dimethyl formamide, dimethyl sulfoxide, methyl ether of polyethylene oxide, if desired.

The reaction mixture, and in the desired molar ratio of starting materials, is normally heated to a temperature within the range of from about 110°C. to about 250°C., preferably about 160°C.–189°C. Further details concerning the normal condensation reaction may be found in the disclosures previously incorporated herein by reference. Generally these reactions are completed when about 25%, by weight, of volatile alkyl halide or alkylene dihalide, based on the initial phosphorus monomer charge, has distilled off.

It has now been found that termination of the condensation reaction when it is only about 35–75% complete, preferably about 40–60% complete, produces a condensed product which will give improved scorch when incorporated in a polyurethane foam formulation, provided the reaction is also carried out in the absence of a nucleophilic initiator, such as sodium carbonate. Such an initiator is commonly used in the prior art synthetic procedures. Generally, the condensation reaction is terminated when the amount of distilled volatile alkyl halide, e.g., ethylene dichloride, or alkylene dihalide which has distilled from the reaction mixture is in the range of about 7–20% by weight of the original monomer charge, preferably about 10–15%.

The product that is formed can be post treated with an alkylene oxide and/or water or alcohol treatment although these post treatments are not normally needed with the product formed by the present invention. These post treatment procedures are described in a number of pending applications and patents including U.S. Pat. No. 3,896,187, Canadian Pat. No. 908,186, U.S. Pat. No. 3,891,727 and copending U.S. Ser. Nos. 473,468, 473,469, 473,470, and 473,471, filed on May 28, 1974. An additional post treatment procedure which could be used is an extraction with an inert organic solvent which is described in applicants' copending U.S. Ser. No. 494,427 entitled "Method of Preparing Stable Condensation Products," filed on even date herewith.

This invention is further illustrated by the following Examples:

EXAMPLE 1

About 2000 g of tris(2-chloroethyl) phosphate and 10% (200 g) of ethylene dichloride, rather than about 0.2% sodium carbonate, were placed in a 2000 ml flask which was then heated at about 140°–180°C. for about 47 hours until 420 g of ethylene dichloride was collected (11% over the 10% catalytic amount originally added). At this point the condensation reaction was about 50% complete. The product had an acid number of 18.8 (ASTM methanol-methyl red method). After treatment for about 41 hours with ethylene oxide at about 100–105°C. the acid number was 2.0 (ASTM methanol-methyl red method).

EXAMPLE 2

The product from Example 1 was incorporated in a polyurethane foam formulation at 10 parts per hundred based on the amount of polyol which was used. The formulation had the following ingredients:

| INGREDIENT | AMOUNT (g) |
|---|---|
| Thanol F-3002 Polyol | 1700 |
| L-548 Silicone | 17 |
| H$_2$O | 68 |
| Niax A-1 catalyst | 1.7 |
| N-ethyl morpholine | 3.4 |
| T$_{10}$ Stannous Octoate (50% in dioctyl phthalate) | 8.5 |
| Toluene Diisocyanate (80% of | |

| -continued | |
|---|---|
| INGREDIENT | AMOUNT (g) |
| 2,4,isomer, 20% of 2,6, isomer) | 885.7 |

The foam was cured for 10 minutes at about 145°C. It showed much less scorch than a foam containing a condensed tris(2-chloroethyl) phosphate formed from a condensation reaction that had been allowed to go to completion and which had been performed with the use of a sodium carbonate initiator. It likewise showed much less scorch than a foam containing a condensed tris(2-chloroethyl) phosphate having a viscosity of about 1250 cps which was formed from a condensation reaction that was performed with use of a sodium carbonate initiator but which was not allowed to go to completion.

What is claimed:

1. In a process for forming a condensation product which is adapted to be used in a polyurethane foam derived from condensing a β-haloalkyl ester of a pentavalent phosphorus acid with itself or with an alkyl ester of a pentavalent phosphorus acid to form a condensation product wherein the improvement comprises terminating the condensation reaction when it is from about 35% to 75% complete and performing the condensation in the absence of a nucleophilic initiator to form a stabilized condensation product.

2. A process as claimed in claim 1 wherein the reaction is terminated when the reaction is from about 40% to about 60% complete.

3. A process as claimed in claim 1 wherein the reaction is terminated when about 7–20% by weight of alkyl halide or alkylene dihalide, based on the weight of the original monomer charge, has distilled from the reaction mixture.

4. A process as claimed in claim 1 wherein the reaction is terminated when about 10–15% of alkyl halide or alkylene dihalide, based on the weight of the original monomer charge, has distilled from the reaction mixture.

5. A process as claimed in claim 1 wherein ethylene dichloride is present when the reaction is begun.

6. A process as claimed in claim 5 wherein the amount of ethylene dichloride is about 10% by weight of the monomer charge which is to be condensed.

7. A process as claimed in claim 1 wherein the condensation product which is treated is selected from the group consisting of the homocondensation product of tris(2-chloroethyl) phosphate, the copolycondensation product of bis(2-chloroethyl) vinylphosphonate and dimethyl methylphosphonate, the copolycondensation product of bis(2-chloroethyl) vinylphosphonate and trimethyl phosphate, the homocondensation product of bis(2chloroethyl) vinylphosphonate, and the copolycondensation product of tris(2chloroethyl) phosphate and dimethyl methylphosphonate.

8. A product formed by the process of claim 1.

9. A stabilized product formed by the process of claim 7.

* * * * *

UNITED STATES PATENT AND TRADEMARK OFFICE
CERTIFICATE OF CORRECTION

PATENT NO. : 3,965,217
DATED : June 22, 1976
INVENTOR(S) : Kyung S. Shim and Edward N. Walsh It is certified that error appears in the above-identified patent and that said Letters Patent are hereby corrected as shown below:

Col. 2, line 2, "160°C-189°C." should be -- 160°C-180°C --

Col. 4, lines 26 and 27, change "(2chloroethyl)" to -- (2-chloroethyl) --.

Signed and Sealed this

Twenty-ninth Day of March 1977

[SEAL]

Attest:

RUTH C. MASON
Attesting Officer

C. MARSHALL DANN
Commissioner of Patents and Trademarks